United States Patent [19]

Muncheryan

[11] 4,093,944
[45] June 6, 1978

[54] SILENT AWAKENING SYSTEM WITH MEANS ADAPTED TO INDUCE SLEEP

[76] Inventor: Hrand M. Muncheryan, 1735 N. Morningside St., Orange, Calif. 92667

[21] Appl. No.: 769,344
[22] Filed: Feb. 16, 1977
[51] Int. Cl.² ............................................. G04C 23/12
[52] U.S. Cl. .................................. 340/279; 340/420; 58/152 B; 340/224
[58] Field of Search ............... 340/224, 279, 331, 407, 340/416, 420; 58/152 B

[56] References Cited

U.S. PATENT DOCUMENTS

| 3,786,628 | 1/1974 | Fossard et al. | 58/152 B |
| 4,028,882 | 6/1977 | Muncheryan | 58/152 B |

Primary Examiner—Alvin H. Waring

[57] ABSTRACT

An electronic system for silently awakening a sleeping person without disturbing others sleeping in the same room and, when desired, for inducing sleep in a person unable to fall asleep naturally is disclosed. The system consists of a signal triggering means comprising either an electric clock or a fire-smoke detection device provided therein with an electronic circuitry having two channels, one channel for developing awakening signals and the other for producing sleep-inducing signals. Said system is further provided with a stimulus-directing means, to be positioned under a sleeping person's pillow for receiving stimuli from said electronic circuitry into said stimulus-directing means and transmitting therefrom continuous as well as recurrent, pulsative motion through said pillow to a person lying thereon, as in sleeping or resting.

20 Claims, 13 Drawing Figures

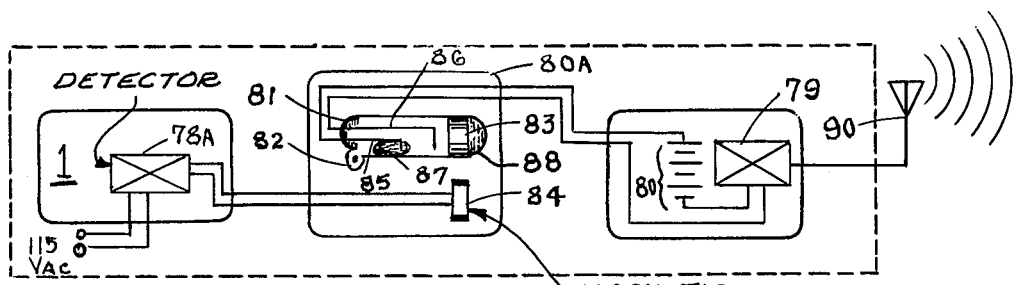
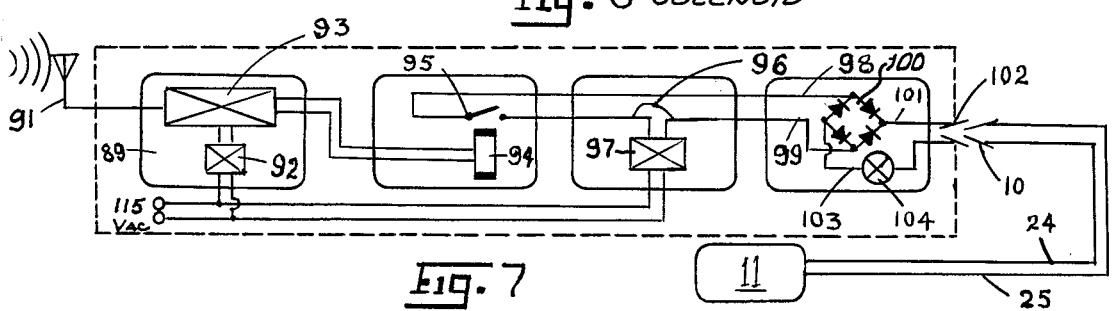
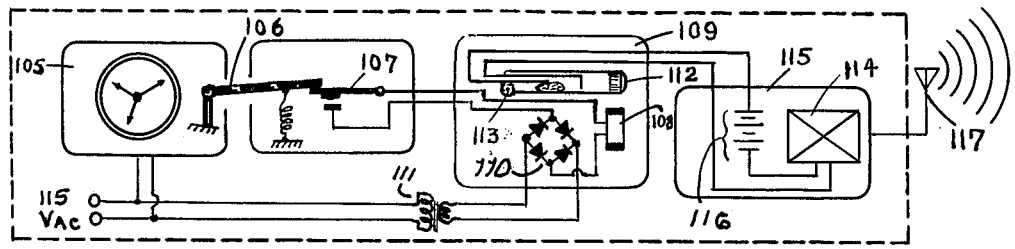
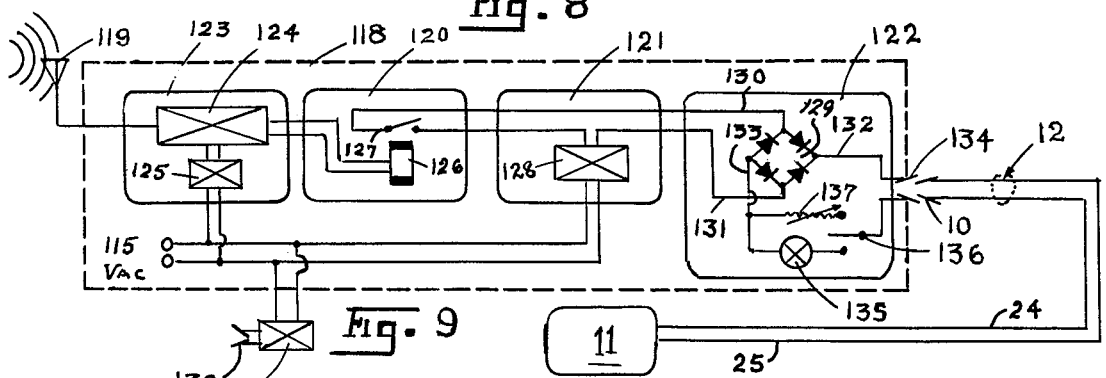
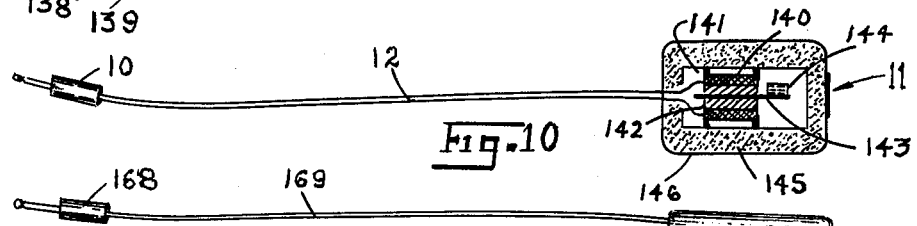
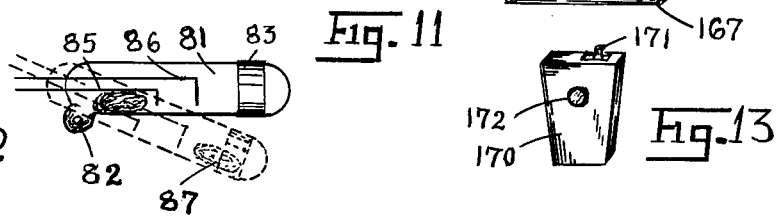
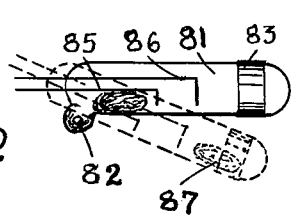
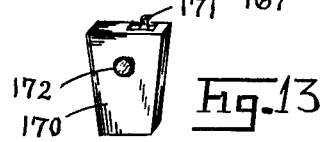

SILENT AWAKENING SYSTEM WITH MEANS ADAPTED TO INDUCE SLEEP

The present invention is generally related to a device for awakening a sleeping person and is more particularly concerned with a device adapted to develop two types of silent signals: one type to awaken a sleeping person and the other type to induce sleep in a person having difficulty in falling asleep.

BACKGROUND OF THE INVENTION

At the present time, the available awakening devices consist of a means for producing sound, such as by a bell, buzzer, siren, or horn. These devices are useful for awakening a group of people located in an area to be covered by a single sound device and that the persons affected by the sound of the device have normal hearing senses, since without hearing the sound the persons cannot wake up by the manner intended. Alarm clocks or fire-smoke detection systems when activated produce a loud shrieking sound to alert persons in the immediate area that they must wake up, as in the case of an alarm clock, or they must run away from the danger locality where a fire, smoke, or any noxious gas has been detected by the detecting device. In the event a deaf person or persons are in the area and are to be alerted, the sound alarm will produce no effect on them since they cannot hear it. A furher shortcoming of an alarm device, as in the case of an alarm clock, when the alarm sounds to awaken the intended person in a bedroom, other persons sleeping in the same room or in adjacent rooms may also wake up, thus somewhat defeating the purpose intended.

There has been a silent method, such as recurrently flashing a light from a clock, to awaken sleeping persons at a set time. However, the difficulty here has been that some persons are not sensitive to light when sleeping, and others may be sleeping on a side remote from the direction of flashing light radiation and, therfore, they may not sense the flashing light. In the case of a flashing light from a smoke detector, no one may even be affected thereby, especially if the detector device is located centrally in a home or similar location for detecting any smoke, fire, or noxious gases and produces a flashing light alarm.

To overcome these shortcomings, the present invention is developed to produce an effective and positive alarm signal which will awaken anyone, whether he is a person of normal hearing, partially deaf, blind, or totally deaf, without limitations of conditions as imposed by the present commercial methods. Also, with the use of the present invention, a person can be alerted of a danger of fire, smoke, or toxic gases occurring remote from his immediate surroundings. The present invention is provided with a detection system which is connected through electric wire or through atmosphere (such as by radio waves) to an awakening unit which is placed under the pillow of the sleeping person for awakening said person when a signal from a fire or smoke detector or from a clock at set time for awakening activates the awakening unit, which is experimentally found to awaken any deaf or normal-hearing person within about ten seconds.

In the case when the awakening signal is transmitted to the awakening unit by radio waves, the fire detector, smoke detector, or the clock is provided with a radio transmitter, which upon receiving a signal from any of these devices it transmits the signal through atmosphere to a radio receiver, which processes the signal into an awakening signal current or sleep-inducing signal current and transmits it to the unit that is placed under the pillow. In such an event, the detector-transmitter system could be located hundreds of feet away from the receiver and more than one person can be provided with a miniature receiver, thereby those persons living in a multistory building, such as a tall hotel building, can all be alerted by the signal (from the transmitter) to make an attempt to leave the place as fast as transportation appliances, such as elevators, are available. At the present time, such hotel fires starting in a lower-level floor will not permit those living in higher-level stories to immediately become conscious of the fire, or noxious gases emanating from a lower level gas storage bins, and many times lives are lost in fires that have started in tall buildings, beacause the sound of the alarm, if any, has not reached the fire victims until it is too late. It thus will be clearly evident that the present silent awakening device located under each individual's pillow will awaken him regardless of the physical condition of the individual; that is, whether the individual can hear, is partially deaf, or totally deaf.

SUMMARY OF THE INVENTION

The present invention is related to my previous invention, Ser. No. 659,323, filed Feb. 19, 1976 and now U.S. Pat. No. 4,028,882. The principal difference between the invention in the pending application and the present application resides in the fact that the present invention includes a radio-wave-transmitting system which broadcasts a signal to an awakener device either from a clock, from a fire or smoke detector, or from any other home security device to a single person or a multiplicity of persons, as desired, and no other persons are disturbed from their sleep while a person in the same room reacts to the signal. In addition, the device is provided with an electronic circuitry, separate from that for awakening, to produce a variable-intensity sleep-inducing radio waves or mechanically produced undulatory stimuli to the same awakener device to activate it in a manner to cause sleep rather than to awaken a person.

Furthermore, the device is provided with the capability of a physical aid means which utilizes the variable sleep-inducing stimuli to administer therapeutic massage to a person's body for alleviating or annihilating temporary muscular aches caused by exposure to cold atmosphere or by accidental spraining a part of a muscle of the body.

To achieve an awakening function at a predetermined time, the principal object of the invention is to provide a clock means to set the time of awakening, an electronic circuitry disposed therein to produce awakening stimuli triggered by the time-setting mechanism of the clock means, and an electronic awakening unit which receives the stimuli produced in said electronic circuitry to transmit them to the sleeping person through the pillow under which the awakening unit is to be placed.

A further object of the invention is to provide pulsations in the stimuli transmitted to the awakening unit so that a repeated pulsing effect is produced in the awakening unit located under the pillow to repeatedly stimulate the sleeper to awaken him in contrast to inducing sleep as by stimulating him by a continuous and constant-level signal which has soothing effect on the nerves thereby inducing sleep in the person using the device.

A still further object of the invention is to isolate the higher-voltage circuitry that develops the awakening stimuli from the awakener unit which is placed under the pillow of a sleeping person, the circuit voltage therein having been reduced to a safe level, such as that furnished by a flashlamp battery, although no contact with the circuit in the awakening unit is possible by the user thereof.

Another object of the invention is the provision of a potting material of electrically insulating character in which all electronic components are potted, whereby it is impossible to make any accidental contact with any parts of the electrical circuitry, including both the higher voltage and the lower voltage sections.

A further object of the invention is the provision therein of a means that can be connected to a fire or smoke detection system and can electrically trigger or actuate said means upon activation thereof by presence of a fire, smoke, or even obnoxious gases, such as carbon monoxide from room heating gases, gasoline fumes from leaky connections, methylene, and sulfide gases which are poisonous to persons inhaling them, said means having been connected to the awakener unit (resonator) through the circuitry developing awakening stimuli, said stimuli being transmitted to said resonator either through electric wires or through radio waves.

One other object of the invention is the provision in the circuitry, triggered by a clock, by a fire, or smoke detection system, of two channels of electric circuits, one channel producing awakening stimuli and the other channel generating sleep-inducing stimuli, each being utilized independently of the other in the resonator unit which may be placed either under a pillow or in the shirt pocket, whichever is considered to be effective for the purpose utilized.

Other objects and the advantages of the invention will become more apparent from the specification taken in conjunction with the accompanying drawings, in which:

FIG. 6 is the block diagram of a smoke and fire detection system with a radio-wave transmitter device for aerial transmission of the smoke or fire signal to a radio receiver.

FIG. 7 is the block diagram of a radio receiver system which receives the radio-wave signals and triggers the awakening circuit shown at the far right block.

FIG. 8 is the partial block diagrams of the clock mechanism and the transmitter, showing the manner of connection of the clock mechanism to the transmitter for producing a single pulse for transmission thereof to the receiver, which contains the awakening means circuitry.

FIG. 9 is the block diagram of the pulse receiver from the transmitter shown in FIG. 8; said pulse triggers either the awakening circuit or the sleep-inducing circuit, shown schematically in the right-hand side block, from which the signal currents are transmitted to the resonator.

FIG. 10 shows the isolated view of the resonator, its cord, and the plug thereof, with the resonator cross-sectioned to show the contructional details thereof.

FIG. 11 is an isolated plan view of a resonator constructionally modified for use as a physical aid means.

FIG. 12 shows the construction of a break-after-make-type mercury switch and the manner of its operation.

FIG. 13 represents the plan view of a miniature radio-receiver-type resonator with an On-Off switch means thereon.

DETAILED DESCRIPTION OF THE INVENTION

Figure 1:
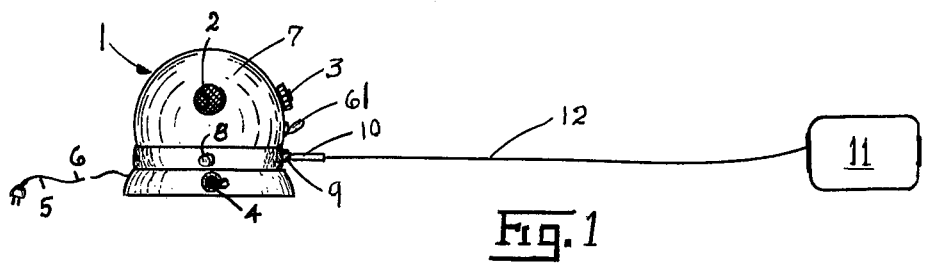
FIG. 1 is a plan view of the smoke or fire detection system connected through an electric cord to the awakening or resonator unit.

Referring to the drawing shown in FIG. 1, numeral 1 designates a smoke or fire detection system, to be referred to hereinafter, for simplicity of reference, as a fire detector device, which is provided with a fire detecting cell 2, which may be either an ionization-type cell, theremostatic cell, or incandescent-filament type; however, I prefer the ionization-type cell because of its high efficiency and controllability. Said fire detector device has a spherical plastic housing for attracting gaseous molecules by electrostatic charge thereof. A 2.5 kilohertz potentiometer 3 connected in the ionization-cell circuitry controls the sensitivity of the detector cell 2, so that gas, smoke, or fume contents in the air down to 0.01 part per million parts in the home atmosphere can be sensed by the cell 2. A switch means 4 is connected in series with the external 115-volt AC current source, from which a current is transmitted through plug 5 and cord 6 into the fire detection circuitry housed in the plastic housing 7, and schematically shown in FIG. 5. The housing 7 may also be made of metal impregnated with a plastic material such as teflon, mylar, and the like. When the external current is turned on with the switch 4, a red indicating light 8 comes on, showing the detection device is receiving current. On the right-side wall of the housing 7 is a jack 9, similar to a telephone switchboard jack; a plug 10 from the resonator 11 plugs into jack 9 for transmitting awakening signals to the resonator 11 through the double-wire electric cord 12.

Figure 2:
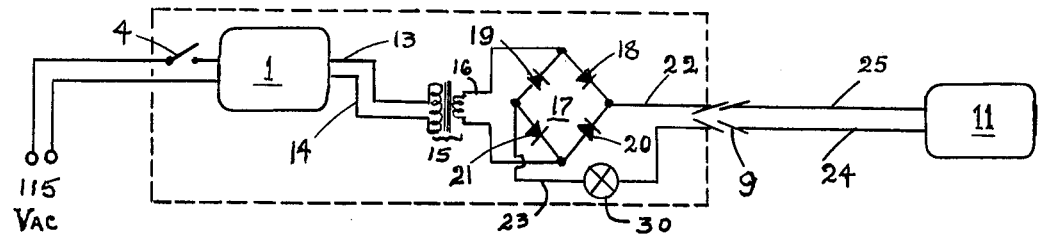
FIG. 2 is a block diagram of the smoke or fire detection system connected to the resonator through a stepdown voltage transformer and a current rectifying section shown in detail.

In FIG. 2, the fire detector device 1 (detailed in FIG. 5), after having been activated by the signal from the detector cell 2, produces a continuous alarm signal which passes through the wires 13 and 14 into a stepdown voltage transformer 15, from which the alternating current of low-voltage side 16 passes into a full-wave rectifier 17, having therein rectifying cells or diodes 18, 19, 20, and 21. The rectifier 17 is a commercial full-wave rectifier and may contain a capacitor in the output side 22 and 23, which side carries a rectified or unidirectional current to the jack 9. Plug 10 from the resonator 11 is plugged into the jack 9 for receiving therefrom the awakening signal and for transmitting it to the resonator 11 through wires 24 and 25, both of which constitute the electric cord 12.

In the operation of the fire detection system, when the detector cell 2 is activated by gaseous particles, such as smoke from a fire, fumes, toxic gas, or the like, as hereinabove stated, the gaseous medium causes ionization in the detector cell 2 and thereby a current passes through detector cell 2 at points 26, 27, 28, and 29, shown in FIG. 5, to be described in detail presently. The amplified current passes through conductors 13 and 14 into the step-down transformer 15 (65 in FIG. 5), whose output is rectified by full-wave rectifier 17. One lead 23 of the output current of the rectifier 17 passes through current interrupter 30, to the jack 9, plug 10, to conductors 24 and 25 and into the resonator 11 and back to the rectifier 17 through the output lead 22.

In the resonator 11, the signal produces at first for 10 to 15 seconds a vibratory motion (see FIG. 10) in the resonator 11 followed by more intense interrupted undulatory motion, which causes the awakening of the sleeping person. The current interrupter 30 can be a commercial-type interrupter of the order of a light flasher used in the passenger cars or trucks; or, it might be a multivibrator-type current interrupter, which employs at least two transistors, two capacitors, and related resistors, all of which come in one commercial unit of any desired current rating. The current interrupter 30 interrupts the current to the resonator 11 from 45 to 60 times per minute, as desired and built during manufacture thereof at the factory. The resonator 11 is placed under the pillow during bedtime, and when an accidental fire occurs in the house, apartment, or dormitory, the resonator 11 becomes activated in the manner described above and awakens the sleeping person within about 10 seconds, as tests on various persons, deaf or of normal hearing, have shown.

Figure 3:
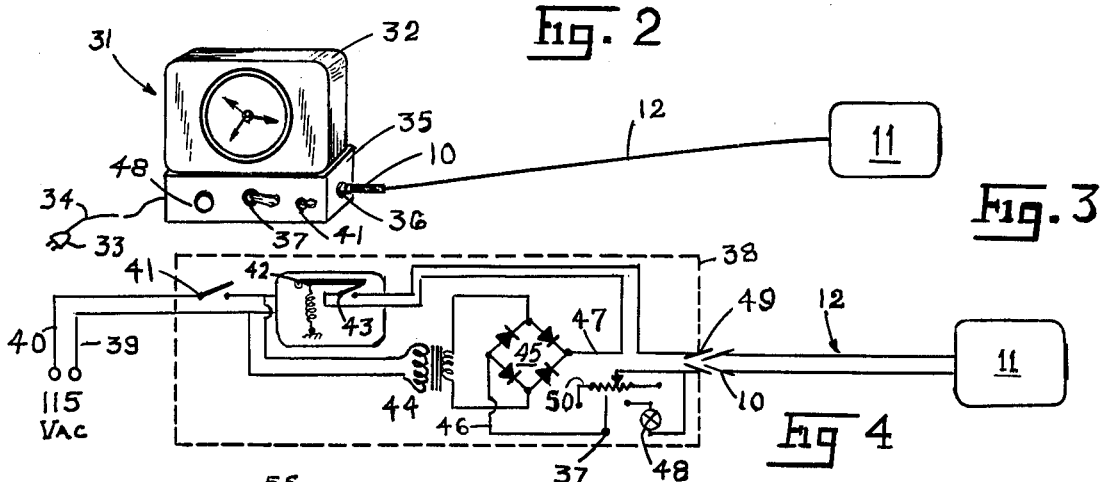
FIG 3 is the plan view of the awakening system using a clock means.
Figure 4:
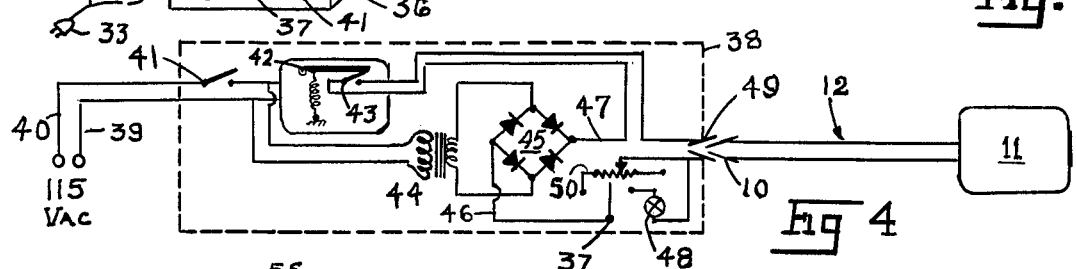
FIG. 4 is the schematic circuit diagram of the awakening system shown in FIG. 3, indicating the manner of signal triggering means of the clock means.

FIG. 3 shows a clock 31, with housing 32, which includes the clock mechanism, a triggering switch, and an electronic circuitry at its base section, all of which are enclosed in the block shown by broken lines in FIG. 4. The clock mechanism receives a 115-volt AC from a household current source through the plug 33 and electric cord 34. An electronic circuitry is provided in the housing 35 located at the base of the housing 32 of the clock mechanism, and a jack 36 is provided in the wall of the housing 35 for accepting the plug 10 of the resonator 11. The electronic circuitry disposed in the housing 35 comprises two circuit channels — one channel producing pulsative awakening signals and the other producing a continuous sleep-inducing signal. The selection of the signals from the circuitry is controlled by a switch 37, one position of which transmits awakening signals and the other position transmits sleep-inducing signals to the resonator 11 through the electric cord 12. The schematic diagram of the electronic circuitry within the housing 35 together with the signal-triggering switch attached to the timing mechanism is shown in FIG. 4.

In FIG. 4, the rectangular box 38 shown by broken lines represents the clock 31 and the electronic circuitry in the housing 35 at the base thereof. The 115-volt AC source transmits a current through the conductors 39 and 40 into the clock 31 for operation of the mechanism thereof. A switch 41 turns on the current to the clock 31. Since the clock employed in this circuit is an alarm clock with its alarm removed, the actuating lever 42 that triggers the alarm is left in the clock mechanism to utilize its movement, when the set time arrives, in closing a switch 43 to the awakening signal circuitry, which is energized by a stepped-down voltage, about 6 to 9 volts, produced by the step-down transformer 44, which is supplied by the 115-volt AC current. The stepped down voltage is rectified by the full-wave rectifier 45 (similar to its counterpart shown in FIG. 2). The output of the full-wave rectifier 45 is fed, in the awakening signal position of the switch 37, through the conductors 46 and 47 and the current interrupter 48 to jack 49, from which the resonator 11 receives the signal current through plug 10 and double-wire electric cord 12. In this position of the switch 37, the awakening signal produced in the electronic circuitry is a series of pulsations occurring 45 to 60 times per minute, depending on the desired interruption rate of the current interrupter 48 constructed during its manufacture.

The present current interrupter 48 has a fine incandescent filament to receive a small current from the conductor 46 which heats a thermostatic switch blade and causes its activation by thermostatic action. The small current passing through the incandescent filament (not shown, since it is a commercial flasher) is fed to the resonator 11 which begins to produce a quivering motion of the entire resonator 11 body; this motion conditions the sleeping person toward awakening him, and when the thermostatic blade is closed, the full rectifier output current flows therethrough and to the resonator 11, thereby producing strong resonant pulsations therein to awaken the sleeping person.

When a person finds it difficult to fall asleep because of nervous aches due to some form of nervous excitement or frustration, the switch 37 is manually positioned in the opposite direction so that the rectified current from the rectifier 45 passes through the variable resistor 50 prior to being led to the resonator 11 through the jack 49. The current through the variable resistor 50 is continuous, without interruption, and when it reaches the resonator 11 it causes the rotor of a small motor in the resonator 11 to rotate continuosuly; however, because of the central shaft of the motor having been provided with a weight projecting unidirectionally and radially to the axis of the motor, the rotor rotates with an unbalanced force directed centrifugally, causing the entire resonator 11 body to undergo an undulatory motion at right angles to its long axis simulating a quivering effect emanated from the resonator 11 which is placed under the pillow of a person lying thereon. The intensity of the quivering effect can be increased or decreased by means of the variable resistor 50, so that the quivering effect on the resonator 11 can be adjusted by the user thereof to a desired intensity. This effect is very soothing with satisfying relaxation to the body, thereby putting the person lying on the pillow with the resonator thereunder to gently go to sleep. If the device is not shut off manually by another person, after the lying person goes to sleep, the soothing effect persists for about one hour, after which time the clock automatically shuts off the current to the resonator, by the retraction of the triggering lever 42 by the gearing action of the clock, an action dominant in all alarm clocks manufactured.

Figure 5:
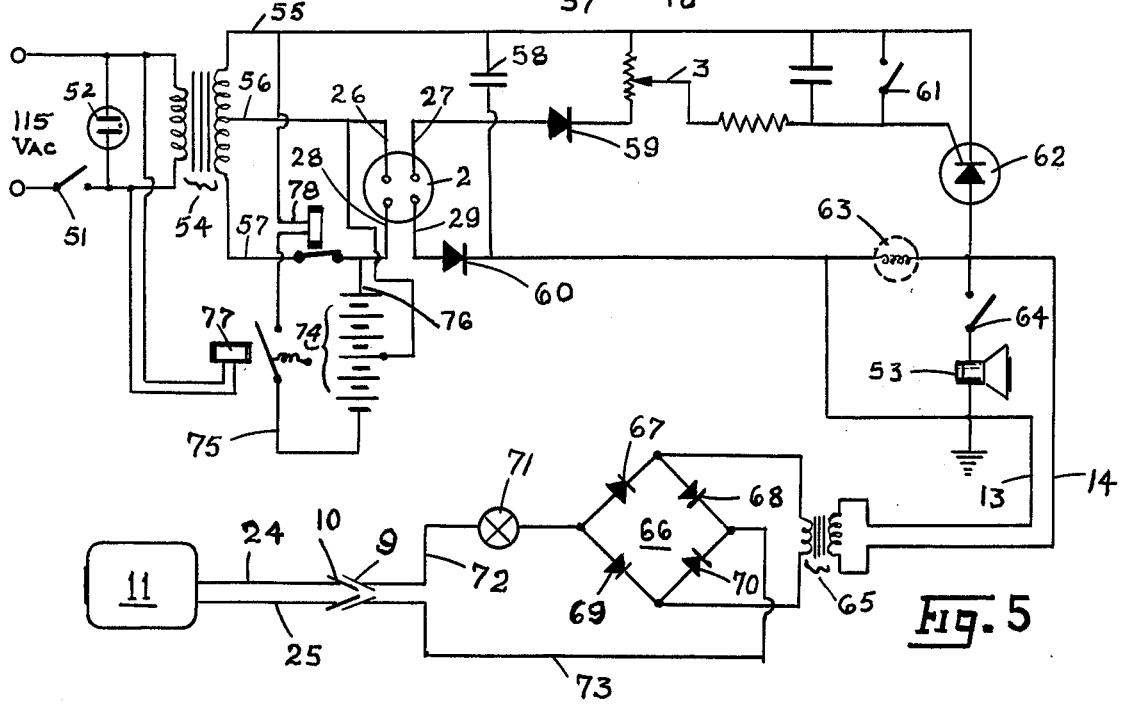
FIG. 5 is the detailed schematic circuit diagram of the smoke or fire detection system shown in FIG. 1, together with the electronic circuitry which produces the awakening signals therein for transmission to the detachable resonator shown at the extreme left side.

FIG. 5 is the complete schematic diagram of the smoke or fire detection system together with the electronic circuitry responsible for the smoke detection and the awakening action of the invention, whose plan view is shown in FIG. 1. In FIG. 5, when the switch means 51 (numeral 4 of FIG. 1) is turned on, permitting the flow of a 115-volt AC current into the detection system, the indicating light 52 (8 in FIG. 1) comes on, showing that the device is operating quiescently, and any smoke, fire, or noxious gas can trigger its alarm device 53 if switch 64 is in closed position. Concurrently, the awakening section can be actuated. The input current from the external 115-volt AC source is applied to a step-up transformer 54, which is center-tapped so that the voltage therein is divided into two equal voltage levels; one level being supplied by a voltage between conductors 55 and 56 and the other level is supplied by the other half of the voltage through conductors 56 and 57.

In the schematic circuit diagram of FIG. 5, the capacitor 58 in conjunction with diodes 59 and 60 produce a half-wave pulsating current. The potentiometer 3 controls the sensitivity of the detector cell 2 as well as performing the zero adjustment function of the system. Switch 61 short-circuits the current to the transistor 62 during adjustment of the detector cell 2 to a relatively pure ambient atmosphere (this adjustment being considered the zero adjustment). This adjustment is made by first rotating the potentiometer 3 until the sound of the siren 53 is heard; the potentiometer then is slowly turned to the opposite direction until the sound barely stops. This point is the zero adjustment point. An optional indicator light indicates at 63 that the smoke or fire detection system is in an operative condition when detection by the cell 2 occurs. The switch 64 shuts off the alarm current from siren 53, especially during nighttime when a deaf person is using the resonator 11 under his pillow. During the daytime, the switch 64 can be turned to ON position so that in the event the detector system is activated it can be heard from inside or outside of the building where it is located.

In operation of the detection system shown in FIG. 5, traces of smoke from an incipient fire, toxic gas such as carbon monoxide, and the like produce a current flow across the cell 2 between leads 26 and 27 and the opposite leads 28 and 29. This current is amplified by the transistor 62 and the amplified current causes the siren 53 to blow if the switch 64 is in closed position. Regardless of the switch 64 position the output current from the transistor 62 flows through conductors 13 and 14 into a step-down transformer 65 (which is exactly the same as transformer 15 of FIG. 2). The transformer's stepped-down pulsating output is impressed on a full-wave rectifier 66 comprising the four diodes 67, 68, 69, and 70. The rectifier 66 (same as 17) current output is unidirectional and is fed through a current interrupter 71 and conductor leads 72 and 73 to the jack 9, plug 10, to the resonator 11, through the conductors 24 and 25 (see FIG. 2). Thus the sleeping person using the awakening resonator 11 is stimulated to become awakened by the action of the pulsating resonator 11. Upon awakening, the plug is removed from the jack 9, if desired.

In the event that the fire destroys the conductors leading from the 115-volt AC current source, the included spare battery 74, whose output conductors 75 and 76 are maintained open by means of the relay 77 energized by the 115-volt AC current when in normal operation, takes over by the closing of the relay 77 and opening of the relay 78 by the battery 74 current passing through the solenoid of relay 78. In this manner, the detector system 1 could be operative at all times regardless of an interruption of the current in the 115-volt AC source.

FIG. 6 is the block diagram of a smoke and fire detection system, wherein the signal from the detector 78A, when activated, is transmitted by a radio transmitter 79, which is powered by a 9-volt battery 80. The transmitter 79 is connected to the smoke-fire detection system 1 through a relay means 80A comprising a break-after-make mercury switch 81, which operates, when activated for a small fraction of a second. This arrangement is necessary because the radio transmitter 79, a commercial sound transmitter operating at frequencies 14 kilohertz to 277 megahertz, requires only a single signal pulse of less than 1 second duration to become activated and thereby to activate its mating receiver tuned to the respective frequencies. The mercury switch 81 is fulcrumed at one end 82 and is provided at the opposite end thereof with a magnetic iron or steel ring 83 so that the switch can be tilted by means of the solenoid 84 for its momentary closure during activation of the solenoid 84 (which has the same constructional form as the related section shown in FIG. 5). The solenoid 84 is connected in series in the output of the fire detection system 1, so that when the detection system is activated the solenoid becomes activated and causes the closure followed by the opening of the mercury switch 81. As will be noted from the diagram of the mercury switch 81, there are two contact electrodes 85 and 86. During normal open-circuit position of the mercury switch 81, there is a pool of mercury 87 in contact with the contact electrode 85, and when the switch 81 is actuated by solenoid 84, the switch 81 tilts clockwise in the diagram, causing the mercury pool 87 to roll and make a momentary contact with the contact electrodes 85 and 86, and to pass on to a neutral position, as shown by broken lines at 88 (see details in FIG. 12). This permits a single pulse to be transmitted from the detection system 1 to the radio transmitter 79, whereupon the transmitter 79 becomes operative and sends out a pulse of radio waves to a remotely located receiver 89, shown as a block diagram in FIG. 7. Numeral 90 represents a signal-broadcasting antenna located internally to the quadrangular broken-line block (housing) of the detection system 1.

FIG. 7 is a block diagram of the receiver system 89 and of the intermediate signal-processing circuits and components electrically disposed between the receiver 89 and the resonator 11. The broadcast, single-pulse signal, is received by receiver 89 through the antenna 91, located internally to its housing, represented by the quadrangular broken-line block. The receiver is energized for quiescent operation thereof by an external 115-volt AC source through a step-down transformer 92, which steps the voltage down to 12 to 24 volts AC, as desired during manufacture thereof. The receiver amplifies the single pulse signal in its amplifying section 93 and transmits the amplified pulse to the solenoid of the latching relay 94, which closes the normally open switch 95 of the low-voltage output section 96 of a step-down transformer 97, which receives an independent current from the 115-volt AC source. The output of transformer 97 is now no more a pulse but a continuous current at about 6 volts AC. This low-voltage current is transmitted through leads 98 and 99 into a current rectifying circuit 100, similar to rectifier 66, for full-wave rectification. One lead 101 of the rectifier 100 output section connects to one side of a jack 102 and the other lead 103 connects to a current interrupter 104 which feeds the recurrently interrupted current to the other side of jack 102 built in the outside wall of the housing of the receiver sytem 89, similar to the jack member 9 shown in FIG. 5. The constantly interrupted current from the jack 102 is transmitted into the resonator 11 through the plug 10 thereof and the leads 24 and 25 constituting the cord 12, FIGS. 1 and 10.

FIG. 8 is the block diagram of a clock-triggered awakening system which transmits its awakening signals or stimuli to the awakening unit 11 (resonator) by means of radio waves. The system principally comprises a clock, represented by the block 105, with a triggering lever 106, which is the same lever that triggers the alarm of the clock when set to a desired time, except that in the present invention the alarm lever 106 turns on the awakening signals, with the original alarm means removed from the clock to make the system operate silently. The lever 106 is mechanically connected to a switch 107, which closes the circuit to a solenoid 108 in the block 109. The solenoid 108 receives its current from the output side of a full-wave rectifier 110 energized by a current from the stepped-down side of a voltage step-down transformer 111, whose primary coil receives a current from the 115-volt AC source. In series with the output circuit of the rectifier 110 is a tiltable, break-after-make mercury switch 112. When the solenoid 108 is energized upon closing of switch 107, as a result of the clock 105 triggering said switch at set time of awakening, the mercury switch 112 tilts clockwise at its tilt axis 113 and closes the circuit momentarily by the movement of the mercury therein from left to right, as detailed in FIG. 12. During its movement from left to right, the mercury within the switch 112 makes a contact between its two contact electrodes, as in mercury switch 81 of FIG. 6, and causes a momentary current flow therethrough; this current in reality is a pulse of less than one second duration, required to activate the transmitter circuit 114, located in block 115 of FIG. 8. When a pulse from block 109 is fed to the transmitter 114, whose circuit is energized by the 9-volt battery 116, a radio pulse of a frequency between 14 kilohertz and 277 megahertz is emanated into the air through the antenna 117. This pulse signal can travel through atmosphere up to 800 feet from the location of the transmitter.

The signal from the transmitter 114 travels to a remotely located receiver, represented by the broken-line rectangular block 118, through the antenna 119, shown in FIG. 9. The receiver automatically tunes itself to the frequency of the transmitter signal. The rectangular block 118 may be considered to be the housing of the receiver, the related components and signal conditioning circuits being marked by blocks 120, 121, and 122. The block 123 comprises the receiver circuit 124, energized by a step-down transformer voltage of 12 or 24 volts, whichever is selected in the particular system during its manufacture. The step-down transformer 125 is energized by a 115-volt AC source, shown in block 118. The pulse received by the receiving circuit 124 is amplified and fed to the solenoid 126 of a latching relay 127, thus closing the relay 127 switch. The relay 127 switch is connected in series with the output circuit of a step-down transformer 128 energized by a 115-volt AC source. The output current of the step-down transformer 128 is about 6 volts AC, although it may be 3 volts or 9 volts, as desired; however, I prefer 6 volts for the present system. The 6-volt AC current is fed into a full-wave rectifier 129, a rectifier made similar to rectifier 66 of FIG. 5, through leads 130 and 131. The rectified output current of rectifier 129 is led, through conductors 132 and 133 to the jack 134 built in the wall of the housing 118. Prior to reaching the jack 134, the rectified current passes through a current interrupter 135, by positioning the switch 136 to make a contact with the interrupter 135 output side. This action causes an interrupted current to flow through jack 134, plug means 10, and the leads 24 and 25 (cord 12 of FIG. 1) into the resonator 11, which then produces a pulsative resonance in the housing thereof to awaken the person sleeping with the resonator 11 under his pillow. When one desires to fall asleep by means of the resonator 11 placed under his pillow, the switch 136 is positioned so that it will contact the variable resistor 137; this action produces a continuous current to flow into the resonator 11.

Since the resonator 11 contains a motorized rotor means rotating with an unbalanced mass therein (see FIG. 10), the housing resonates continuously in an undulatory motion, which action is both soothing and relaxing, thus inducing sleep in the person utilizing the device. The resistor 137 is manually adjusted from the exterior of the device to suit the intensity of the undulatory motion to his liking. The sleep-inducing section of the device operates until it is turned off manually by a non-sleeping person, or when it is left alone the clock in block 105 will automatically turn it off after about one hour of operation, a characteristic possessed by almost all alarm clocks manufactured today. Since the alarm clock minus the alarm is being used in this system, this feature of the clock is taken advantage of by its turning off of the sleep-inducing section of the system. The clock can perform this action because in restoring the lever 106 to its original position, it produces another single pulse in the transmitter by the opening of switch 107.

For sick room service, or elderly people who require service from household members, a socket 138 is provided in the 115-volt circuit of the awakening system, whereby any auxiliary lamp with a cord and plug can be inserted into the socket 138 for receiving current thereinto; a current interrupter 139 is provided in series with the light circuit so that the light can flash periodically to draw attention from the household occupants.

FIG. 10 represents the resonator 11 with its plug 10 and cord 12. The resonator 11 is shown in sectional view to describe its contents. The cord 12 (wires 24 and 25) is connected to the stator coil 140 of a motor 141 to energize it into rotation. The rotor 142 is provided with an axial rod 143 rotative thereby. At the terminal section of rod 143 is a metal weight 144 extending radially to only one side of rod 143. The weight 144 causes an unbalance in the rotation of the rod 143, thereby producing an undulatory vibration of the motor 141 during its operation. The motor housing is embedded in an insulating potting material 145 whereby the operational vibration of the motor 141 is transmitted to the exterior of the housing 146. When a recurrent or interrupted current is fed to the motor 141 from the awakening system, the interrupted current causes a further and more intensive undulatory motion of the motor 140; thus, the two vibratory motions are superimposed mechanically on each other, producing a resultant pulsative resonance in the bulk of the housing. This resonance awakens the person sleeping with the resonator 11 under his pillow.

With a continuous current flowing into the resonator 11 from the, for example, section 137, the resonator operates with a constant undulatory or vibratory motion; this motion is further exaggerated by a slight bend of the rod 143 near the base of the weight 144. By sliding the variable resistor 137, a vibratory motion can be selected whereby said motion can be utilized to massage the body or to cause gentle soothing in the body, when the resonator is placed under a pillow and the person's head lies on it, so that the resultant effect is to induce sleep in the person lying on the pillow. For such a double function of a resonator, FIG. 11 shows the resonator designed in the form of a wand 167. The internal construction of the wand 167 is exactly the same as that shown in the resonator 11 of FIG. 10. Since the motorized portion of the resonator in the wand 167 takes a fraction of the entire wand housing, the remainder of the housing is filled with an electric insulating potting material to give the motor mounting rigidity in the tubular housing as well as increasing the weight of the wand 167, increasing the momentum of the rotary motion within the wand 167. The plug 168 and the cord 169 as shown in FIG. 11 are also similar to those respective parts shown in FIG. 10. The advantage of the wand 167 design is that it permits the convenient use of the wand on the face, arms, chest, or any other part of the body requiring relaxation.

FIG. 12 shows the constructional view of the break-after-make mercury switch 112, with the mercury 87 moving to a neutral position at the extreme end of the device housing. In moving from its original neutral position, shown by the solid lines in the figure, the mercury makes a contact with the electrode points 85 and 86 prior to rolling to the position shown by broken lines in FIG. 12. As stated earlier, this single contact establishes a single pulse necessary to operate the radio transmitter 79 of FIG. 6 or 114 of FIG. 8.

In FIG. 13 is shown a miniature radio receiver 170, which contains all the elements of the radio receiver shown in FIG. 7 or FIG. 9 in a miniaturized circuit similar to commercial microelectric components arranged on a small printed circuit board, and the transistors, capacitors, diodes, and resistors necessary in a radio receiver circuit are deposited on a silicon or sapphire wafer in vacuum. In this way, the receiver can be made smaller than an ordinary cigaret package and can be carried in a shirt pocket for alerting the bearer of a fire from a distance up to 800 feet. The miniature device can also be placed under the pillow of a sleeping person to wake him up; in a household of several people, each can use the device under his pillow to receive alerting signals from a fire, smoke, or noxious gases. Since the device will operate at low direct current voltages, a 9-volt radio battery is utilized, eliminating the use of any step-down transformers as used in other receivers shown in the present drawings since devices shown in the figures are less costly to make. A switch on radio receiver 170, designated by numeral 171, turns on or off the current supplied from the 9-volt battery, in the housing 170. A knob 172 varies the sensitivity of reception as well as the intensity of the vibratory current therein, which in circuit design and operation is exactly the same as the system in FIG. 9. This receiver can be employed to become activated by either a fire-detection system, gas detection system, or by a clock mechanism shown in the various figures in the drawings, the transmission of signal being from remotely located systems transmitting by radio waves.

The disclosure of the invention described herein represents the preferred embodiments of the invention; however, variations thereof, in the form, construction, and arrangement of the various electronic components thereof and the modified applications of the invention are possible without departing from the spirit and scope of the appended claims.

I claim:

1. A silent awakening system with means adapted to induce sleep in a person, said system comprising: a first means for producing an electrical signal and being energized for quiescent operation thereof from an external source of current, a second means for receiving and directing said electrical signal through an electrical transmission medium to an electrical signal receiving means electrically coupled thereto; said second means having therein a circuit adapted to process said electrical signal into a continuous flow of direct current, and means disposed in said circuit for channeling said direct current into two circuit sections; one of said circuit sections is adapted to conduct said continuous flow of direct current and having therein a control means to vary the current flow therethrough, and the other circuit section having means therein to convert said continuous direct current into recurrent pulsations; electrical means for selecting one of said circuit section at a time and to direct the current from the selected circuit section into a physical aid means in detachable, electrical connection with said electrical means for selecting one of said circuit sections at a time; an electric motive means disposed in said physical aid means and receiving a current from the selected circuit section for producing in said physical aid means a mechanical tremor of varying intensities comprising of two types of actions, one of which being an awakening action produced by said means adapted to convert said continuous direct current into recurrent pulsations, and the other type of action being a sleep-inducing operation produced by said control means by varying the intensity of the current therethrough and thereby the intensity of tremor produced in said physical aid means to suit the user thereof, said two types of mechanical actions occurring independently of each other therein; and, a current outlet means, disposed in the circuit of said second means and connected to receive a current from an external 115-volt source, is provided with a current interrupter in the circuit thereof to produce therein a recurrently interrupted electrical current and to transmit said current to a standard electric lighting means electrically connected to said current interrupter, causing said standard electric lighting means to emit a recurrently flashing light therefrom.

2. A silent awakening system with means adapted to induce sleep in a person as described in claim 1, wherein said first means for producing an electrical signal is a fire-smoke detection means connected to an external source of current for energization thereof and having in the circuit thereof a nonconducting electric means adapted to receive gaseous fumes through the atmosphere from a burning fire and to become an electric conducting means, and means connected to said electric conducting means and adapted to receive current therefrom for electrically processing and then transmitting said current into an electrically operative resonator to produce therein a pulsative mechanical action for awakening a sleeping person using said electrically operative resonator under his bed pillow.

3. A silent awakening system having means adapted to induce sleep in a person as defined in claim 1, wherein said means for directing the electrical signal through an electrical transmission medium comprises a clock mechanism, means to open and close an electrical circuit mechanically connected to said clock mechanism; and means adapted to rectify a current, receiving an alternating current from an external source, the rectified current output thereof is connected to said means adapted to open and close an electrical current, said last means receives said rectified current output for transmission thereof through said electrical medium to an externally located electrical means electrically connected thereto to produce mechanical motion therein.

4. A silent awakening system with means adapted to induce sleep in a person as defined in claim 1, wherein said means for directing the electrical signal through an electrical transmission means is a transmitter means having therein an electric signal amplifier adapted to receive and amplify said electrical signal, means disposed in said transmitter means to convert said electrical signal into a continuous flow of current of constant amplitude and to feed said current of constant amplitude into an electrical rotating means electrically connected thereto to produce a constant mechanical motion, in said electrical rotating means, directed at right angles to the central axis thereof.

5. A silent awakening system having means adapted to induce sleep in a person as described in claim 1, wherein said means for channeling said direct current into two circuit sections is an electrical double-throw switch means disposed between said two circuit sections.

6. A silent awakening system with means adapted to induce sleep in a person as described in claim 1, wherein said physical aid means comprises a housing having therein means operable by a stepped-down low-voltage current supplied thereto from an external current source, said last means adapted to produce an oscillatory motion, in said housing, when energized by said low-voltage current supplied thereto, means for substantially affixing said means adapted to produce an oscillatory motion of said housing, whereby the effect of said oscillatory motion can be effectively transmitted to the exterior of said housing.

7. A silent awakening system with means adapted to induce sleep in a person as described in claim 1, wherein said means for producing an electric signal comprises: a housing having therein a step-up transformer receiving current from an external source through a control means disposed in series relation therewith, a smoke and fire detection means connected to said step-up transformer and adapted to generate an electrical signal when a smoke atmosphere is sensed thereby, and means to amplify an electric signal, receiving said electrical signal from said smoke and fire detection means, to amplify said electrical signal and to direct the amplified signal current into a sound-producing means to alert persons of the presence of smoke and fire in the environment of said smoke and fire detection means; means connected electrically in parallel relation to said sound-producing means and adapted to step down the voltage of said amplified signal current and to feed said last current to a means for rectifying said amplified signal current; and, means disposed in the output circuit of said means for rectifying said amplified signal current to convert the output current thereof into a pulsative unidirectional current and to feed said pulsative unidirectional current into an electrically motive means disposed in a housing and mechanically connected thereto for producing a mechanical turbulence therein.

8. A silent awakening system with means to induce sleep in a person as described in claim 1, wherein said means for producing an electrical signal is a clock means having therein an alarm-producing mechanical section with an alarm-triggering lever, the alarm-producing means thereof having been removed for silent operation of said clock means; a current rectifying means is disposed in the housing of said clock means and receives a current from an external source of high-voltage alternating current and converts said alternating current into a low-voltage direct current, said current rectifying means having an output-current section provided with an open-circuit switch means in mechanical contact with said alarm-triggering lever, which closes said switch means when a preset time has elapsed in said clock means; said output-current section is provided in the current thereof with two branch circuits, one of said branch circuits having therein a variable resistor for producing a varying-intensity unidirectional current therein, the other branch circuit having therein a current interrupter for producing a pulsative unidirectional current; a double-throw current-switching means adapted to selectively contact one of said branch circuits at a time is disposed across said two branch circuits; a resonator means operative from a current from either one of said two branch circuits, and produces therein a sleep-inducing effect, when receiving a current from said branch circuit having a variable resistor therein, and it produces an awakening effect when receiving a current from said branch circuit having therein a current interrupter; said resonator means is placed under the pillow of a sleeping person to transfer thereto either said sleep-inducing effect or said awakening effect through said pillow, depending on the position of said double-throw current-switching means disposed across said two branch circuits.

9. A silent awakening system with means adapted to induce sleep in a person as defined in claim 1, wherein said means for producing an electrical signal is a smoke and fire detection system operable by an electric current provided thereto from an external current source, said smoke and fire detection system having a spherical housing with a smoke detector disposed centrally on the surface thereof, said spherical housing having an electrostatically sensitive surface to attract gaseous particles and smoke to its curved surface and thereby to the smoke detector, disposed thereon, an electrical circuit disposed in said spherical housing and connected to said smoke detector; a current amplifying means provided in said electrical circuit to receive an electric signal from said smoke detector upon activation thereof and to amplify said electric signal, a fire alerting means consisting of a sonorous and a silent alarm means disposed in parallel relation to each other in the current output section of said current amplifying means, the current output section of said current amplifying means putting out a relatively high-voltage alternating current, a step-down transformer disposed in electrically parallel relation to said sonorous alarm means, for stepping down the alternating current voltage; a rectifying circuit disposed at the stepped-down current output section of said transformer to rectify said stepped-down alternating current prior to transmitting the rectified current thereof to said silent alarm means; said sonorous alarm means comprising a siren and said silent alarm means comprising a miniature housing including therein an electrically oscillatory means to produce a recurrent pulsative motion in said housing and to communicate said motion to a user of said silent alarm means, thereby alerting the user silently to the occurrence of a fire detected by said smoke and fire detection system.

10. A silent awakening system with means adapted to induce sleep in a person as described in claim 1, wherein said means for producing an electric signal comprises a smoke and fire detection system energized by an external source of electric current for its quiescent operation, said smoke and fire detection system having an ionization-type gaseous-particle detector in the electrical circuit thereof and when activated by smoke from a fire produces a small signal current therein, an amplifying circuit in said smoke and fire detection system connected to said ionization-type gaseous-particle detector to receive said small signal current produced thereby and to amplify said signal current for transmission to a silent alarm system electrically connected thereto and physically located under a pillow of a sleeping person; said silent alarm system comprises a miniature housing enclosing therein means for producing an oscillatory motion of said housing when said last means receives a current from said amplifying circuit upon activation of said smoke and fire detection system.

11. A silent awakening system having means adapted to induce sleep in a person as defined in claim 1, said system comprising a fire-detection system provided therein with a radio transmitter operable at frequencies between 14 kilohertz and 277 megahertz, said fire-detection system comprising a fire-detector means activated by smoke from a fire occurring in the vicinity of said fire-detection system to produce an electrical signal in said fire-detector means, a current amplifier disposed therein and connected to said fire-detector means to amplify the electrical signal received therefrom and to transmit it into said radio transmitter, from which the amplified signal is transmitted through atmosphere to a remotely located radio receiver tuned to the frequencies of said radio transmitter; said radio receiver is provided with a current from an external current source for its quiescent operation, and has a latching relay connected to the output circuit thereof; said radio receiver upon receiving an electrical signal from said radio transmitter energies said latching relay which is in series connection with the output ciruit of a step-down voltage transformer receiving an alternating current independently of the current energizing said radio receiver; the output current from said step-down voltage transformer is led into a full-wave rectifying circuit disposed in said radio receiver, the output conductor leads of said full-wave rectifying circuit having therein a current interrupter for producing therethrough a recurrently flowing current and feeding said current to a current receptacle disposed in the wall of the housing enclosing said fire-detection system; and, a physical aid means comprising an electrically oscillatory means therein receives said recurrently flowing current through said current receptacle to actuate said electrically oscillatory means and thereby to cause a pulsative, oscillatory motion of said physical aid means, which in use is placed under the pillow of a sleeping person for awakening said person when a destructive fire occurs in an area in the vicinity of said fire-detection system.

12. A silent awakening system with means adapted to induce sleep in a person as defined in claim 11, wherein said physical aid means is provided with an elongated tubular housing tapering at one end to a spherical configuration, and at the opposite end having means adapted to transmit an energizing current from the full-wave rectifying circuit into said elongated tubular housing; said elongated tubular housing is provided therein with an electrically actuable means electrically coupled to said means adapted to transmit energizing current thereinto for producing, in said electrically actuable means, an oscillatory motion at right angles to said elongated tubular housing, a momentum-producing means adapted to substantially attach said electrically actuable means to the internal wall of said elongated tubular housing to communicate said oscillatory motion thereto and to increase the effectiveness of the oscillatory motion thereof.

13. A silent awakening system with means adapted to induce sleep in a person as defined in claim 1, wherein said silent awakening system is provided with an electric battery to automatically take over the function of the external source of current when the electric conductor leads thereof become destroyed by an accidental fire, the manner of substitution of the electric battery for the external source of current being performed by the provision of a normally open first relay switch in series relation to the circuit of said electric battery, said first relay switch being maintained open by the magnetic action of the solenoid of said first relay switch, which receives a current from said external source of current when said silent awakening system is energized thereby, a second relay disposed in series with the battery output leads and whose switch means provided therein being retained in a normally closed position by a spring means attached to said switch means of said second relay, whereby when said electric conductor leads are destroyed by fire, the solenoid of the first relay becomes nonconductive, thus permitting the switch means thereof to close by the action of the spring thereof, and the switch means of said second relay to open by the action of the solenoid of said second relay, which then carries a current from the battery, thus disconnecting the current therein from the external source of current and connecting said battery to the circuit of said slent awakening system for operation thereof.

14. A silent awakening system with means adapted to induce sleep in a person as described in claim 11, wherein said radio transmitter is activated to transmission by a single pulse of signal less than one second duration for the proper operation of the remotely located radio receiver tuned to the frequencies of said radio transmitter; a normally open-circuit mercury switch is disposed in the housing of said radio transmitter and receives an energizing current from a battery provided in the circuit of said radio transmitter; said open-circuit mercury switch having a ring of magnetizable material at the proximal end thereof and at the distal end it is provided with a fulcrum to permit the rotation thereon of said mercury switch, which has therein two contact electrodes, one of which is in contact with the mercury disposed therein during the normally open-circuit position of said mercury switch; a magnetic solenoid energizable from the battery disposed therein is positioned adjacent to said ring of magnetizable material and is activated when the fire-detection system senses smoke from the immediate vicinity thereof, said magnetic solenoid then attracts the magnetizable ring and causes the tilting of said mercury switch and thereby momentary closing thereof by the mercury making a contact between the two contact electrodes therein during rolling of the mercury from one end of the mercury switch to the other end, thus establishing a single pulse in the radio transmitter.

15. A silent awakening system with means adapted to induce sleep in a person as described in claim 2, wherein said fire-smoke detection means connected in the circuit of said silent awakening system is provided therein with an electric potentiometer having a manually controllable knob built into the wall of the housing of said silent awakening system for making an initial zero adjustment, manually from the exterior thereof, of said fire-smoke detection means to ambient noncontaminated atmosphere where said silent awakening system is to be employed; said electric potentiometer further controls the sensitivity of said fire-smoke detection means for the detection thereof of any gaseous contaminants in the air in a quantity dangerous to human life.

16. A silent awakening system with means adapted to induce sleep in a person as described in claim 11, wherein said remotely located radio receiver tuned to the frequencies of said radio transmitter is a pocket pager having a miniature radio receiver circuit therein provided with a miniature battery to energize said radio receiver upon receiving thereby a radio-wave signal from said radio transmitter; a current amplifying means disposed in said radio receiver circuit for amplification of said radio-wave signal; the amplified signal current is then led into a vibratory means provided in the housing of said miniature radio receiver and thereby to activate said vibratory means therein for alerting the bearer of said miniature radio receiver of the occurrence of a fire in the area surrounding said radio transmitter.

17. A silent awakening system with means adapted to induce sleep in a person as described in claim 1, said system comprising two principal electrical units, a first electrical unit and a second electrical unit, separated one from the other through an electrical transmission medium electrically connecting said units theretogether, the first of said electrical units comprises a means for developing an electric signal, means for producing a unidirectional current from said electric signal, and means for transmitting said unidirectional current to said second electrical unit, which is provided with a housing having therein an off-axis rotary means for the activation thereof; said off-axis rotary means produces an undulatory motion in said housing and transmits said undulatory motion to the exterior thereof.

18. A silent awakening system with means adapted to induce sleep in a person as described in claim 17, wherein said first electrical unit comprises a clock means having therein a release lever actuable by the mechanism of said clock means upon elapsing a set time in said clock means, a normally open mercury switch means having two electrode contacts therein and being in mechanical relation with said release lever and actuable thereby, a current rectifying means disposed therein with said normally open mercury switch connected in the output circuit thereof, and a radio transmitter disposed in the housing of said clock means and having a battery in series relation with said normally open mercury switch, whereby upon elapsing of said set time said release lever becomes actuated, thereby tilting said normally open mercury switch and causing the mercury pool therein to roll from the initial position thereof at one end to the opposite end of said mercury switch and making a momentary contact between said two electrode contacts therein, said momentary contact producing a single signal by the closure of the battery circuit therein and thereby energizing said radio transmitter, which transmits the single signal to a remotely stationed radio receiver tuned to the frequency of said radio transmitter signal.

19. A silent awakening system with means adapted to induce sleep in a person as described in claim 18, wherein said radio transmitter transmitting a single signal to a remotely stationed radio receiver tuned to the frequency of said single signal is adapted to generate said single signal at frequencies ranging from 14 kilohertz to 277 megahertz, to which frequencies said remotely stationed radio receiver has been adapted to be tuned selectively by means of an automatic control disposed in the circuit thereof.

20. The radio receiver described in claim 19 is provided in the circuit thereof with an electrical processing circuit which receives the single signal from the radio transmitter and converts it into a continuous direct current, a first means disposed at the current output section of said electrical processing circuit to control the intensity of the current passing therethrough, a second means connected electrically in parallel relation to said first means to convert the continuous direct current received thereby from said electrical processing circuit into a recurrently flowing unidirectional current, a third means disposed in the current output section of said electrical processing circuit and adapted to selectively transmit therethrough a current received thereby from either said first means or said second means, and a fourth means having therein an electrically motive means to receive current produced in said first means through said third means for producing a vibratory motion therein that induces sleep in a person, and when said fourth means receives a current from said second means through said third means it produces therein a recurrently pulsative vibration that produces an awakening action in a person using said fourth means.

* * * * *